United States Patent [19]
Koide

[11] Patent Number: 5,557,047
[45] Date of Patent: Sep. 17, 1996

[54] METHOD AND APPARATUS FOR ULTRASONIC WAVE MEASUREMENT

[75] Inventor: Makoto Koide, Shizuoka, Japan

[73] Assignee: Fuji Ultrasonic Engineering Co., Ltd., Hamamatsu, Japan

[21] Appl. No.: 189,873

[22] Filed: Feb. 1, 1994

[30] Foreign Application Priority Data

Feb. 10, 1993 [JP] Japan .................................. 5-044371

[51] Int. Cl.⁶ .......................... G01N 29/02; G01N 29/18
[52] U.S. Cl. .......................... 73/597; 73/24.06; 73/54.41; 73/61.79; 73/64.53
[58] Field of Search .............................. 73/19.03, 24.01, 73/24.06, 54.24, 54.41, 61.45, 61.49, 61.75, 61.79, 64.42, 64.53, 597, 602, 629

[56] References Cited

U.S. PATENT DOCUMENTS

| | | |
|---|---|---|
| 3,697,936 | 10/1972 | Zacharias, Jr. et al. .................. 73/597 |
| 3,715,709 | 2/1973 | Zacharias, Jr. et al. .................. 73/597 |
| 4,095,457 | 6/1978 | Koda et al. ............................. 73/64.53 |
| 5,125,273 | 6/1992 | Negita ..................................... 73/597 |
| 5,214,955 | 6/1993 | Yost et al. .............................. 73/61.75 |

*Primary Examiner*—Hezron E. Williams
*Assistant Examiner*—Rose M. Finley
*Attorney, Agent, or Firm*—Dvorak and Traub

[57] ABSTRACT

A method and apparatus for ultrasonic wave measurement wherein the time interval between like order echoes selected with respect to adjacent transmitted waves is controlled to be equal to an integral multiple of a period ($t_3$) of a continuous oscillation wave. In addition, the time interval between like order echoes adjacent to each other that are selected with respect to the same transmitted wave is controlled to be equal to the period ($t_3$) of the continuous oscillation wave. The period ($t_3$) of the continuous oscillation wave that is obtainable under the above controlled state, is measured, and the result of the measurement is used as ultrasonic wave propagation time for obtaining the absolute sound velocity.

3 Claims, 4 Drawing Sheets

METHOD AND APPARATUS FOR ULTRASONIC WAVE MEASUREMENT

BACKGROUND OF THE INVENTION

1. Field of the Invention

The present invention relates to a method and an apparatus for ultrasonic wave measurement and, more particularly, to a method and an apparatus for ultrasonic wave measurement, which is suitable for measuring the velocity of sound propagated through a medium subject to measurement such as a gas, a liquid, or a solid. The method and apparatus are suitable for determining the components, concentrations, modulus of elasticity of a gas or a liquid and for determining the modulus of elasticity, strength, fatigue, stress history, life, of a solid.

2. Description of the Background Art

In the method of ultrasonic wave measurement, multiple echoes that are generated successively on the basis of a wave transmitted from an ultrasonic wave transmitter through a medium subject to measurement, the echoes are received in an ultrasonic wave receiver, and an absolute velocity (V) of sound propagated through the medium is determined from a propagation time ($t_t$) obtained from the echoes and a propagation distance (L).

Among the prior art methods of measuring the propagation time are a sing-around method, an overlap method, and a superimpose method.

The sing-around method has heretofore been used extensively because of its stability of measurement and demands for automatic measurement. However, this method is susceptible to influence from external factors. The overlap and superimpose methods are less subject to influence from external factors but, they do not permit automatic measurement due to prohibiting factors such as cost, and technical difficulties.

SUMMARY OF THE INVENTION

It is an object of the present invention to obtain automatic measurement of ultrasonic wave propagation time with high accuracy and high stability.

According to the invention, there is provided a method of ultrasonic wave measurement in which multiple echoes generated successively on the basis of waves transmitted from an ultrasonic wave transmitter through a medium under measurement are received in an ultrasonic wave receiver to determine an absolute velocity (V) of sound propagated through the medium on the basis of a propagation time ($t_t$) determined from the echoes and a propagation distance (L). The method comprises selecting at least two multiple echoes of specific orders for each transmitted wave, outputting a continuous oscillation wave, controlling a time interval between like order echoes selected with respect to adjacent transmitted waves to be equal to an integral multiple of a period ($t_3$) of the continuous oscillation wave, controlling a time interval between echoes adjacent to each other selected with respect to the same transmitted wave to be equal to the period ($t_3$) of the continuous oscillation wave, measuring the period ($t_3$) of the continuous oscillation wave obtainable in the above controlled state, and using the result of the measurement as the propagation time ($t_t$) for determining the absolute velocity (V) of sound.

According to the invention, there is provided an apparatus for ultrasonic wave measurement in which multiple echoes generated successively on the basis of waves transmitted from an ultrasonic wave transmitter through a medium under measurement are received in an ultrasonic wave receiver to determine an absolute velocity (V) of sound propagated through the medium on the basis of a propagation time ($t_t$) determined from the echoes and a propagation distance (L). The apparatus comprises a continuous oscillation controller for selecting at least particular order two of a plurality of multiple echoes generated for each transmitted wave, outputting a continuous oscillation wave, controlling a time interval between like order echoes selected with respect to adjacent transmitted waves to be equal to an integral multiple of a period ($t_3$) of the continuous oscillation wave, and controlling a time interval between echoes adjacent to each other selected with respect to the same transmitted wave to be equal to the period ($t_3$) of the continuous oscillation wave, a time measurement circuit for measuring the period ($t_3$) of the continuous oscillation wave as a propagation time ($t_t$) while the controls by the continuous oscillation controller is in force, and an operational circuit for determining the absolute sound velocity by using the result of measurement by the time measurement circuit.

According to the invention, one of several ultrasonic transmitters and receivers may be used. The ultrasonic transmitter and receiver shown in FIG. 4A comprises an ultrasonic wave transmitting section 1A and an ultrasonic wave receiving section 1B spaced apart therefrom a distance L. The ultrasonic transmitter and receiver shown in FIG. 4B comprises an ultrasonic wave transmitter/receiver section 1 and a reflector 4 spaced apart therefrom a distance L. The ultrasonic transmitter and receiver shown in FIG. 4C comprises an ultrasonic wave transmitter/receiver section 1 and a solid reflector 4 spaced apart therefrom a distance L. The ultrasonic transmitter and receiver shown in FIG. 4A is applicable to a gas, liquid and solid medium, and that shown in FIG. 4B is applicable to a gas and liquid and that shown in FIG. 4C is applicable to a solid medium respectively.

FIG. 4D is a schematic view showing transmitting and receiving of electric signal and ultrasonic wave signal to the transmitter/receiver in case of FIG. 4B. In FIG. 4D, ultrasonic wave transmitter/receiver section 1 is composed of an acoustic transducer 2 and an acoustic transmission plate 3 and the acoustic transducer 2 does not directly touch the medium under measurement. The acoustic transducer is adhered to acoustic transmission plate (or pressed and fixed by couplant to acoustic transmission plate). The acoustic transmission plate of ultrasonic wave signal can be varied corresponding to medium under measurement. Since the acoustic transducer needs not to touch the medium under measurement, an ultrasonic wave transmitter/receiver (sensor) using this acoustic transducer can easily realize corrosion resistance, heat resistance and pressure resistance. These resistances are essential to industrial instrument.

When an electric pulse burst signal is impressed on the acoustic transducer, an ultrasonic wave signal is caused to propagate through the acoustic transmission plate into the medium under measurement. The signal is reflected at the reflector to propagate back through the medium under measurement and pass the acoustic transmission plate to the acoustic transducer (the first echo $W_{J11}$). On the other hand, an echo which reflects at the boundary between the acoustic transmission plate and the medium under measurement is caused to propagate three times through the medium under measurement and reflected at the reflector to propagate back through the medium under measurement four times and pass the acoustic transmission plate to the acoustic transducer (the second echo $W_{J12}$).

As set forth above, the ultrasonic wave signal propagating through the medium under measurement is repeatedly reflected between the acoustic transmission plate and the reflector and becomes a multiple echo and holds the state until acoustic energy vanishes. Shown at 101 in FIG. 2 are transmitted and received waves which are detected in a measuring circuit connected to the ultrasonic transmitter/receiver. Labeled $W_{S1}$ and $W_{S2}$ are burst waves which are transmitted intermittently at a time interval $t_1$. Labeled $W_{J11}$, $W_{J12}$, . . . are multiple echoes (a first echo $W_{J11}$, a second echo $W_{J12}$, . . . ) which are produced successively on the basis of the wave $W_{S1}$, and labeled $W_{J21}$, $W_{J22}$, . . . are multiple echoes (a first echo $W_{J21}$, a second echo $W_{J22}$, . . .) produced successively on the basis of the wave $W_{S2}$. According to the invention, these multiple echoes are utilized to determine the propagation velocity of an ultrasonic wave through the medium under measurement.

In the ultrasonic wave measurement system, there exists an electric transmission cable between the acoustic transducer and the measurement circuit. Also, there exists an acoustic transmission plate for propagating acoustic signal between the acoustic transducer and the medium under measurement.

In FIG. 4D, electric signal propagation time between electric terminal 28 and the acoustic transducer is $t_E$, ultrasonic wave signal propagation time among the acoustic transducer, the adhered layer and acoustic transmission plate is $t_a$. The wave propagation time $t_w$ passing through other than medium under measurement can be obtained by the following equation.

$$t_w = t_E + t_a \quad (1)$$

Therefore, in the FIG. 2 (101), the time ($t_{SJ11}$) between the transmitted wave ($W_{S1}$) and the first echo ($W_{J11}$) can be obtained by the following equation.

$$t_{SJ11} = 2t_w + t_t \quad (2)$$

And also the time ($t_{SJ12}$) between the transmitted wave ($W_{S1}$) and the second echo ($W_{J12}$) can be obtained by the following equation.

$$t_{SJ12} = 2t_w + 2t_t \quad (3)$$

By the above equations (2) and (3), the time interval ($t_t$) between the first echo and the second echo can be obtained as follows.

$$t_{SJ12} - t_{SJ11} = t_t \quad (4)$$

By this equation (4), if the time interval $t_{SJ12} - t_{SJ11}$ between the first and second echoes $W_{J11}$, $W_{J12}$ is to be measured to cancel the time $t_w$, the time ($t_t$) of propagation of the ultrasonic wave through the sole medium under measurement can be obtained with the cancellation of the time $t_w$. It is thus possible to obtain an absolute measurement of the propagation time other than a relative measurement thereof. On the other hand, by the equation (2), the time interval ($t_{SJ11}$) between the transmitted wave and the first echo is not in conformity with the ultrasonic wave propagation time ($t_t$) through the medium ($t_{SJ11} > t_t$). If the absolute measurement of the ultrasonic wave propagation time $t_t$ is obtainable, the velocity V of propagation of the ultrasonic wave is obtainable simply with equation (5) below by accurately measuring the propagation distance L.

$$V = 2L/t_t \quad (5)$$

According to the invention, for the absolute measurement of the propagation time $t_t$, a continuous oscillation wave is produced such that its period $t_3$ is equal to the time interval $t_t$ between the first and second echoes $W_{J11}$ and $W_{J12}$. The propagation time $t_t$ is obtained by measuring the period time $t_3$. FIG. 2 is a waveform chart in a state when the oscillation period $t_3$ and propagation time $t_t$ become equal. Labeled 105 in FIG. 2 is the continuous oscillation wave with the period $t_3$ equal to the propagation time $t_t$. The propagation time $t_t$ can be measured by measuring the period $t_3$ of the wave 105. The waveform 105 is in phase with waves Wf11 and Wf12 whic are obtained by shaping the waves $W_{J11}$ and $W_{J12}$ of the waveform 101. To provide this state, it is necessary to satisfy two conditions given by the following equations (6) and (7).

$$t_1 = t_2 = t_3 \times m \text{ (m being an integer)} \quad (6)$$

$$f_{out} = 1/t_3 \quad (7)$$

where $t_1$ is the time interval between the transmitted burst waves $W_{S1}$ and $W_{S2}$, $t_2$ is time interval between the first shaped echo $W_{f11}$ based on $W_{S1}$ and the first shaped echo $W_{f21}$ based on $W_{S2}$, and $t_3$ is the period of the continuous oscillation wave. The value m, an integer, is determined by such factors as the attenuation of the multiple echoes (such as $W_{J11}$, $W_{J12}$, $W_{J13}$. . . ). If the attenuation of the multiple echoes is not too much, the value of m is increased to reduce the influence of the multiple echoes.

To simultaneously satisfy the equations (6) and (7), according to the invention, the time interval between like order echoes (such as $W_{J11}$) and $W_{J12}$) that are selected with respect to adjacent transmitted waves is controlled to be equal to an integral multiple of the period $t_3$ of the continuous oscillation wave, and also the time interval ($t_t$) between echoes adjacent to each other (such as $W_{J11}$ and $W_{J12}$) that are selected with respect to the same transmitted wave is controlled to be equal to the period $t_3$ of the continuous oscillation wave. The condition of the equation (7) cannot be satisfied solely but is satisfied simultaneously with the condition of the equation (6). By measuring the period $t_3$ of the continuous oscillation wave when the propagation time $t_t$ and the continuous oscillation wave period $t_3$ thus become equal, the propagation time $t_t$ can be measured as $t_t = t_3$. Thus, the propagation time $t_t$ can measured.

By using a method in which a plurality of periods of the continuous oscillation wave are measured with a counter using a reference clock and averaged to obtain the cycle time $t_3$, it is possible to obtain measurement with a higher accuracy than the reference clock frequency. This is an effective feature of the invention. In the measurement by the simple pulse method, the accuracy of measurement can not be increased by averaging, but it depends on the frequency of the basic clock. As shown above, the propagation time $t_t$ in the equation (5) is obtained in the above way.

The propagation distance L in the equation (5), on the other hand, is obtained as follows. The distance L is changed with temperature. The change with thermal temperature is based on the coefficient of thermal expansion of the material that determines the propagation distance. The change in the length L of the material including the coefficient of thermal expansion is given by the equation (8):

$$L = Lo(1 + \alpha \theta) \quad (8)$$

where $\alpha$ is the coefficient of thermal expansion, $\theta$ is the temperature, and Lo is the length at the reference temperature.

Here, $\alpha$ can be predetermined for it is the coefficient of thermal expansion of the material determining L. Lo has a value peculiar to the ultrasonic transmitter/receiver, which is determined by fluctuations at the time of the manufacture and can be readily measured using water. In other words, the velocity of sound through water is known as a literature value as shown by the equation (9).

$$V = 1402.736 + 5.033580 - 0.0579506\theta^2 + \\ 3.31636 \times 10^{-4}\theta^3 - 1.45262 \times 10^{-6}\theta^4 + \\ 3.0449 \times 10^{-9}\theta^5 \quad (9)$$

Thus, it is possible to determine the value of L from the temperature θ of certain water, the velocity V of sound through the water based on the literature value and the actual measurement of the propagation time and also determine the value of $L_0$ which is a peculiar value to the ultrasonic transmitter/receiver from the equation (8). Once the values of $L_0$ and α are determined in this method, the value of L can be determined by measuring the temperature of the ultrasonic transmitter/receiver.

With the above measurements of the propagation time $t_t$ and propagation distance L, the velocity V of ultrasonic wave can be measured with high accuracy and high stability using the equation (5).

BRIEF DESCRIPTION OF THE DRAWINGS

The present invention will be more fully understood from the detailed description given below and from the accompanying drawings which should not be taken to be a limitation on the invention, but for explanation and understanding only.

In the drawings.

DESCRIPTION OF THE PREFERRED EMBODIMENT

Figure 1:
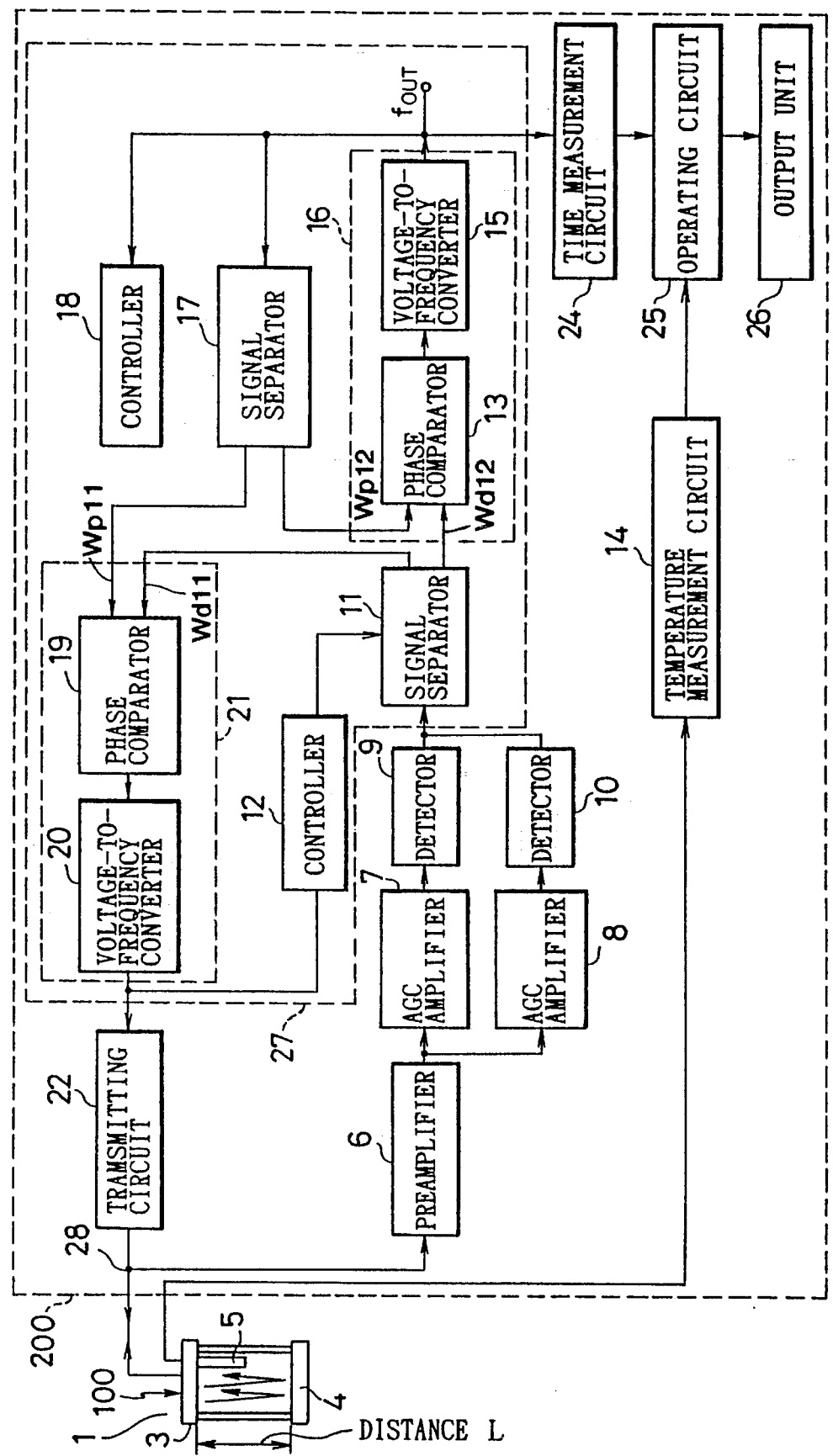
FIG. 1 is a block diagram showing an example of apparatus for ultrasonic wave measurement.

Referring to FIG. 1, there is shown an apparatus for ultrasonic wave measurement which comprises an ultrasonic wave transmitter/receiver 100 and a measuring circuit 200.

In the ultrasonic transmitter/receiver 100, an acoustic transmission plate 3 and a reflector 4 are disposed such that they face each other and are separated a distance L, which is filled with a medium under measurement (either gas, liquid or solid). The ultrasonic transmitter/receiver 100 further includes a temperature sensor 5.

Waves transmitted from the acoustic transducer 2 in the ultrasonic transmitter/receiver 100 are propagate into the medium through the acoustic transmission plate 3, and are repeatedly reflected between the acoustic transmission plate 3 and reflector 4 until they are depleted acoustic energy due to attenuation of the multiple ultrasonic echoes into the medium. The ultrasonic wave transmitter/receiver 100 receives this multiple echoes.

The measuring circuit 200 includes a preamplifier 6, AGC amplifiers 7 and 8 with gate, detectors 9 and 10, a continuous oscillation controller 27, a transmitting circuit 22, a temperature measurement circuit 14, a time measurement circuit 24, a digital operational circuit 25, and an output unit 26.

The preamplifier 6 amplifies the multiple echoes.

The AGC amplifiers 7 and 8 amplify only the first echoes ([WJII] $W_{J11}$, $W_{J12}$) and second echoes ($W_{J12}$, $W_{J22}$) among the multiple echoes generated for each transmitted burst wave. At this time, the AGC amplifiers 7 and 8 function to hold a constant signal amplitude level irrespective of echo level variations with changes in the medium (see waveforms 102 and 103).

The detectors 9 and 10 are basically analog comparators. Their reference level is set such that the first and second echoes are both compared at the same waveform position to convert the signals having been amplified in the AGC amplifiers 7 and 8 to a single pulse digital signal (see waveform 104).

The digital signal thus obtained is input to the continuous oscillation controller 27 to be processed in the manner as shown by the operations (1) to (5) for conversion to a continuous oscillation signal at frequency $f_{out}$ with the ultrasonic wave propagation time $t_t$ equal to the period $t_3$. The continuous oscillation signal thus obtained is input to the time measurement circuit 24.

Figure 2:
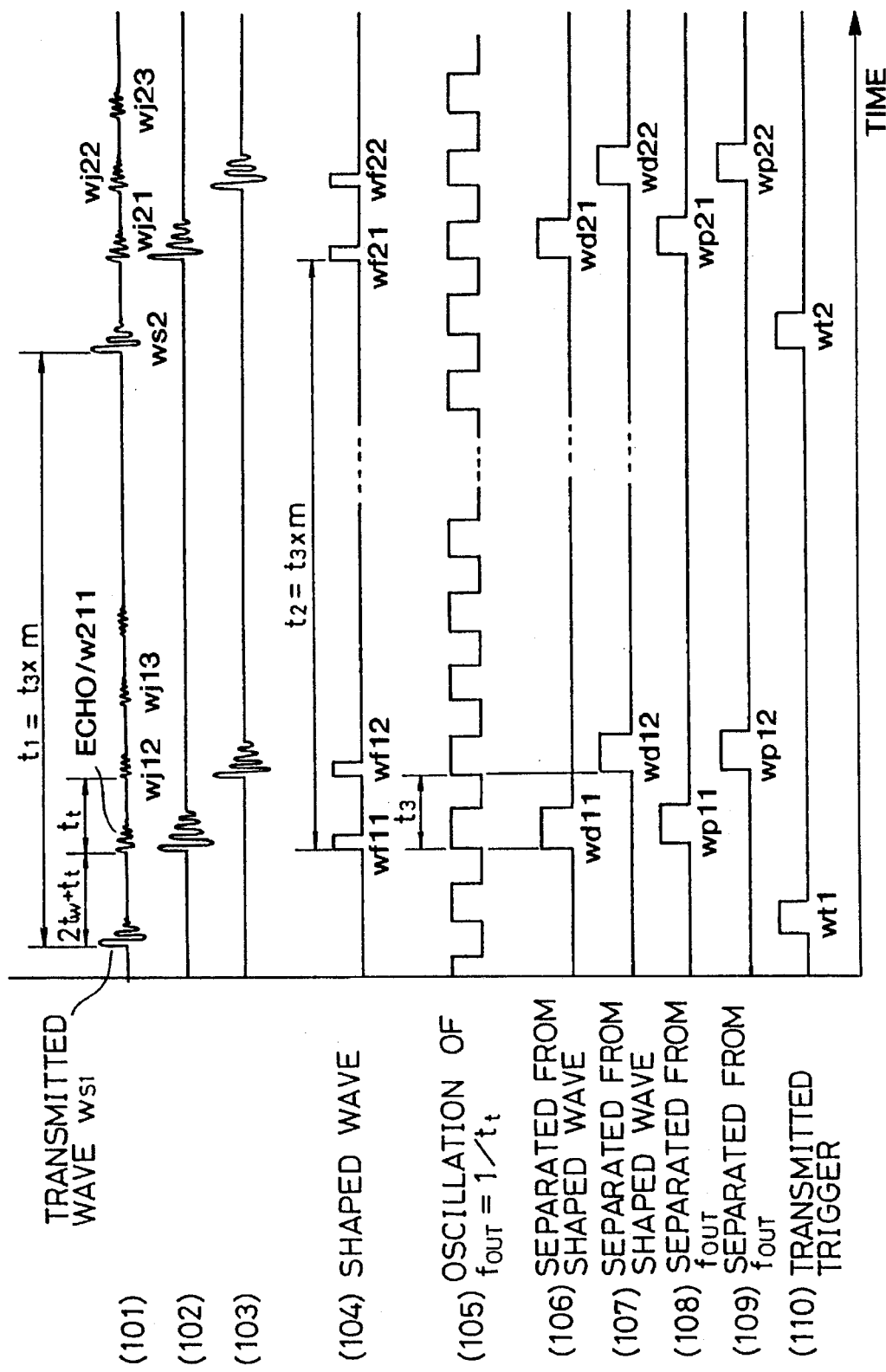
FIG. 2 is a waveform chart for the ultrasonic wave measurement apparatus.

(1) The digitized first and second received wave signals, shown at 106 and 107 in FIG. 2, are separated in the signal separator 11 to be input to phase comparators 19 and 13 in phase-locked loops (PLLs) 21 and 16, respectively.

(2) The continuous oscillation signal 105 which is output from a voltage-to-frequency converter 15 is frequency divided by m to be input as waveform 108 from a signal selector 17 to the phase comparator 19.

(3) The phase comparator 19 compares the waveforms 106 and 108. To make the phase of these waveforms coincide, a voltage-to-frequency converter 20 is controlled such that the time interval $t_1$ between the first echoes $W_{J1}$ and $W_{J3}$ or like order among the echoes ($W_{J11}$, $W_{J12}$) and ($W_{J21}$, $W_{J22}$), selected with respect to the adjacent transmitted bursts $W_{S1}$ and $W_{S2}$ is equal to m times the period $t_3$ of the continuous oscillation wave. The output signal of the voltage-to-frequency converter 20 becomes a trigger signal 110, and an ultrasonic wave signal 101 is transmitted from the transmitting circuit 22. Since the waveforms 106 and 108 are made to coincide in phase, we have $t_1=t_2=t_3 \times m$, and the condition of the above equation (6) is thus satisfied.

(4) The continuous oscillation signal 105 output from the voltage-to-frequency converter 15, like the signal 108, is frequency divided by m to be output as signal 109 delaying by one period from the signal 108 from a signal selector 17 to the phase comparator 13.

(5) The phase comparator 13 compares the signals 107 and 109 and controls the voltage-to-frequency converter 15 such as to make these signals coincide in phase. Thus, $W_{d11}$ and $W_{p11}$ in the respective waveforms 106 and 108 are made to coincide in phase, and $W_{p12}$ is delayed by one cycle of the continuous oscillation signal frequency $f_{out}$ of $W_{p11}$ and made to coincide in phase with $W_{d12}$. Thus, the period $t_3$ of the continuous oscillation wave 103 becomes equal to the time interval $t_t$ of the echo of the signal 101. (That is, the time interval $t_t$ between the adjacent first and second echoes $W_{J11}$ and $W_{J12}$ that are selected with respect to the same transmitted burst wave $W_{S1}$ becomes equal to the period $t_3$ of the continuous oscillation wave.) The ultrasonic wave propagation time $t_t$ thus can be measured by measuring the period of the continuous oscillation wave $f_{out}$.

The continuous oscillation controller 27 continuously repeats the above operations (1) to (5) for each transmitted burst wave.

The time measurement circuit 27 comprises a reference clock and a counter. To increase the accuracy of the time measurement of the period $t_3$ of the input signal, the circuit 24 measures the time of a predetermined number of periods (for instance 1,000 periods) and calculates the average of a predetermined number of periods (for instance 1,000 periods) set in the succeeding stage digital operational circuit 25.

The digital operational circuit 25 calculates the temperature of the propagation medium according to the signal from the temperature measurement circuit 14 and calculates the temperature-compensated ultrasonic wave propagation distance L from the calculated temperature. From the above calculation result, the ultrasonic wave propagation velocity is calculated using the equation (7). The result is output from the output unit 26.

The control operation of the continuous oscillation controller 27 constituting the measuring circuit 200 will now be described in detail with reference to FIG. 3.

Figure 3:
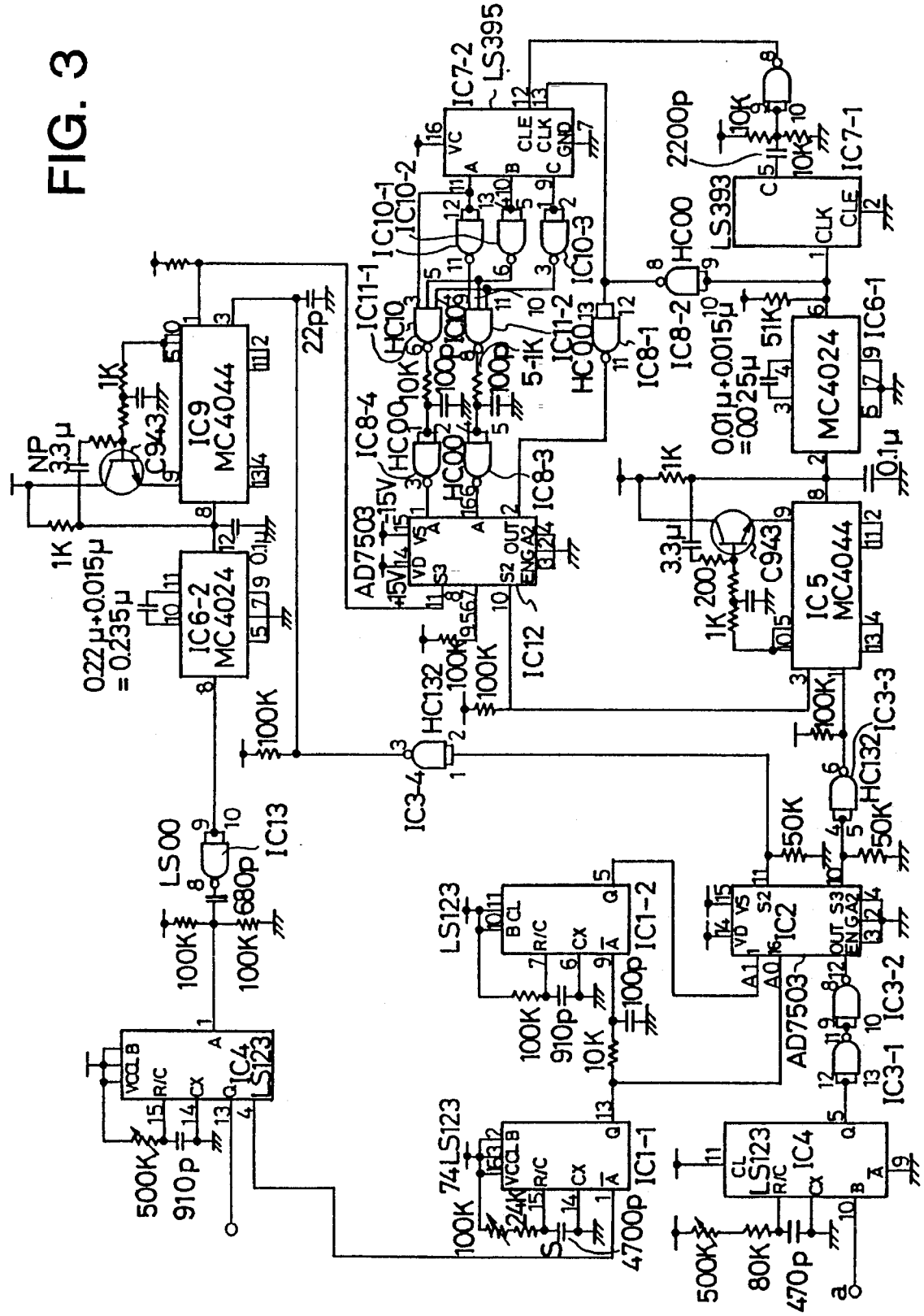
FIG. 3 is a circuit diagram showing a continuous oscillation controller.
Figure 4A:
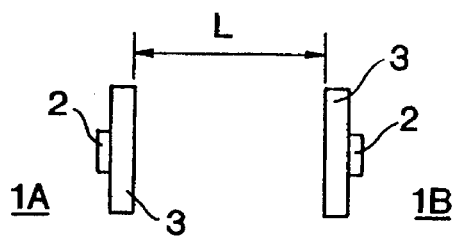
FIGS. 4A, 4B, 4C and 4D are schematic views showing ultrasonic wave transmitter/receivers.
Figure 4B:
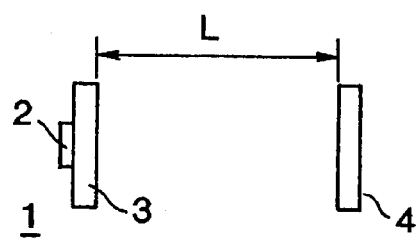
Figure 4C:
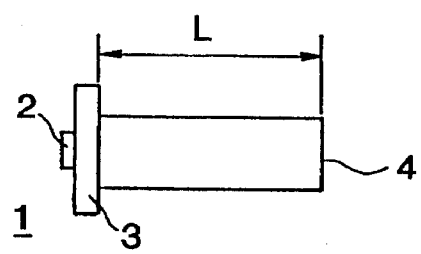
Figure 4D:
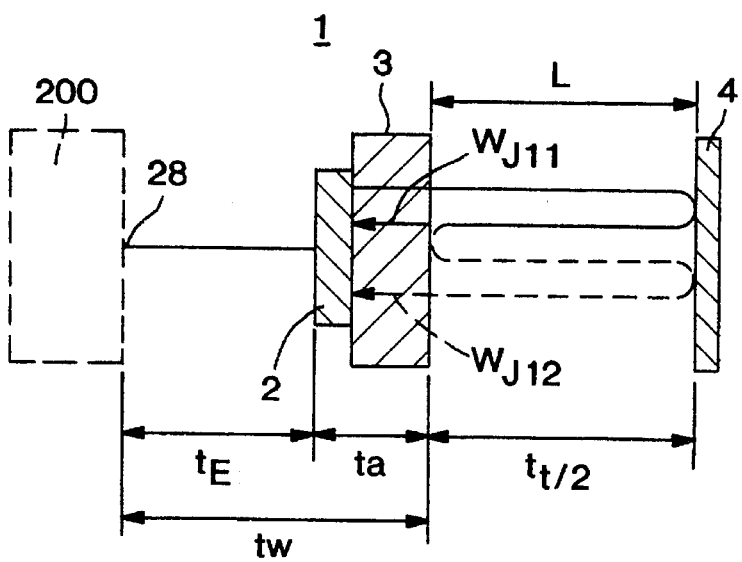

The first and second received waves as ultrasonic waves are passed through the AGO amplifiers 7 and 8, and a digitized pulse wave (see waveform 104) from 20 the detectors 9 and 10 is input to a section a shown in FIG. 3. This pulse waveform is input to a signal selector IC2 which is controlled by control circuits IC1-1 and IC1-2. Digitized waveforms $W_{f12}$ and $W_{f22}$ (see waveform 104) which are obtained from the second received waves, are output to S3 of IC2 to become waveforms $W_{d12}$ and $W_{d22}$ (see waveform 107), which are coupled through a buffer IC3-3 to a phase comparator ICS. Designated at IC6-1 is a voltage-controlled oscillation IC oscillating at a frequency corresponding to a DC output voltage of IC5 (see waveform 105). This continuous oscillation wave is passed through buffers ICS-1 and IC8-2 to be output signal selector IC12.

Counters IC7-1 and IC7-2 for setting the period $t_1$ of the transmitted signal (see waveform 101) to m times the propagation time through frequency division by m and control circuits IC10-1, IC10-2, IC10-3, IC11-1, IC11-2, IC8-3 and IC8-4, control IC12 such that the output S2 of the signal selector IC12 is a signal which is lagging in phase behind the output S3 by one period of oscillation of voltage-controlled oscillator IC6-1 (see waveform 108, 109). The m value of the frequency division counter may be set to a desired value, for instance, 4, 8 or 16. It is set such that the multiple echoes are not affected by the propagation distance L, attenuation of the propagation medium, etc.

The output S2 of signal selector IC12 is input to phase comparator IC5 for phase comparison with the output of buffer IC3-3. Phase comparator IC5 controls the output of IC5 and DC voltage such that the signals are brought to be in phase, and also controls next stage voltage-controlled oscillator IC6-1. The output from S3 of signal selector IC12 is input to phase comparator IC9. Phase comparator IC9 phase compares the first received wave of ultrasonic wave output from buffer IC3-4 to the digitized signal, and phase comparator IC9 control the output DC voltage such that the input waveforms are in phase and also controls the frequency of next stage voltage-controlled oscillator IC6-2. The fall signal of the oscillation signal of IC6-2 (see waveform 110) becomes a trigger signal to control the timing of the ultrasonic wave transmission signal. A state in which the input phases of IC5 and IC9 are locked to the same phase, corresponds to a state in which the ultrasonic wave propagation time $t_t$ (see waveform 101) and the period of the oscillation frequency $f_{out}$ of voltage-controlled oscillator IC6-1 are equal to each other. Thus, by measuring the oscillation period $t_3$, it is possible to measure the ultrasonic wave propagation time $t_t$ and also obtain automatic measurement of the absolute ultrasonic wave propagation velocity.

Now, the effects of the embodiment will be described.

1. The invention concerns an absolute sound velocity measurement method, in which only the time of propagation through a medium under measurement is measured. Thus, the propagation time measurement is free from error that may result from the presence of a cable or like signal propagation means between the ultrasonic wave transmitter/receiver and the measuring circuit. It is thus possible to cope with changes in the signal propagation means such as cable length.

Moreover, since it is capable of interposing the acoustic transmission plate between the acoustic transducer and the medium under measurement, the condition in using the acoustic signal transmitter/receiver (sensor) (e.g., corrosion resistance, heat resistance and pressure resistance) can be increased.

2. Since the propagation time is converted to the frequency of the continuous oscillation wave with the propagation time as the period, it is possible to obtain improvement of the accuracy of measurement by averaging the measurement time, which has not been effective so much with the pulse method.

3. Because of the absolute sound velocity measurement method, it is possible to obtain a highly accurate measurement in a wide range. In addition, it is possible to obtain a fast sound velocity measurement as an automatic measurement.

4. It is possible to readily determine the temperature compensation factor (or power generation compensation factor, etc.) of the propagation distance peculiar to the ultrasonic wave transmitter/receiver, which is very effective in maintenance such as the replacement of the ultrasonic transmitter/receiver.

As has been described in the foregoing, according to the invention, it is possible to obtain automatic measurement of an ultrasonic wave propagation time with high accuracy and high stability.

Although the invention has been illustrated and described with respect to several exemplary embodiments, it should be understood by those skilled in the art that the foregoing and various other changes, omissions and additions may be made to the present invention without departing from the spirit and scope thereof. Therefore, the present invention should not be understood as limited to the specific embodiment set out above but to include all possible embodiments which can be embodied within a scope encompassed and equivalents thereof set out in the appended claims.

What is claimed is:

1. A method of ultrasonic wave measurement, in which multiple echoes generated successively on the basis of waves transmitted from an ultrasonic wave transmitter through a medium under measurement are received in an ultrasonic wave receiver to determine an absolute velocity (V) of sound propagated through the medium on the basis of a propagation time ($t_t$) determined from the echoes and a propagation distance (L), the method comprising steps of:

selecting at least two of multiple echoes of specific order for each transmitted wave;

outputting a continuous oscillation wave;

controlling a time interval between like order echoes selected with respect to adjacent transmitted waves to be equal to an integral multiple of a period ($t_3$) of the continuous oscillation wave;

controlling a time interval between echoes adjacent to each other selected with respect to the same transmitted wave to be equal to the period ($t_3$) of the continuous oscillation wave;

measuring the period ($t_3$) of the continuous oscillation wave obtainable in the above controlled state; and using the result of the measurement as the propagation time ($t_t$) for determining the absolute sound velocity (V).

2. An apparatus for ultrasonic wave measurement, in which multiple echoes generated successively on the basis of waves transmitter from an ultrasonic wave transmitted through a medium under measurement are received in an ultrasonic wave receiver to determine an absolute velocity (V) of sound propagated through the medium on the basis of a propagation time ($t_t$) determined from the echoes and a propagation distance (L), the apparatus comprising:

a continuous oscillation controller means for selecting at least particular order of two of a plurality of multiple echoes generated for each transmitted waves;

outputting a continuous oscillation wave;

controlling a time interval between like order echoes selected with respect to adjacent transmitted waves to be equal to an integral multiple of a period ($t_3$) of the continuous oscillation wave; and controlling a time interval between echoes adjacent to each other selected with respect to the same transmitted wave to be equal to the period ($t_3$) of the continuous oscillation wave;

a time measurement circuit means for measuring the period ($t_3$) of the continuous oscillation wave as the propagation time ($t_t$) while the controls by the continuous oscillation controller means is in force; and an operational circuit means for determining an absolute sound velocity by using the result of measurement by the time measurement circuit.

3. An apparatus for ultrasonic wave measurement as claimed in claim 2, in which an acoustic transducer comprising the ultrasonic wave transmitter and the ultrasonic wave receiver, faces to the medium under measurement by interposing an acoustic transmission plate adhered to the acoustic transducer.

* * * * *